(12) United States Patent
Newkirk et al.

(10) Patent No.: US 7,735,788 B2
(45) Date of Patent: Jun. 15, 2010

(54) PATIENT CARE EQUIPMENT MANAGEMENT SYSTEM

(75) Inventors: David C Newkirk, Lawrenceburg, IN (US); Mark A Graham, Springsboro, OH (US); Steven J Schwartz, Oxford, OH (US); Michael E Cerimele, Indianapolis, IN (US); John W Ruehl, Shelbyville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 44 days.

(21) Appl. No.: 11/737,298

(22) Filed: Apr. 19, 2007

(65) Prior Publication Data

US 2007/0187559 A1 Aug. 16, 2007

Related U.S. Application Data

(63) Continuation of application No. 11/422,476, filed on Jun. 6, 2006, now Pat. No. 7,216,382, which is a continuation of application No. 10/802,289, filed on Mar. 17, 2004, now Pat. No. 7,065,812.

(60) Provisional application No. 60/455,621, filed on Mar. 18, 2003, provisional application No. 60/510,756, filed on Oct. 13, 2003.

(51) Int. Cl.
*A47K 1/04* (2006.01)

(52) U.S. Cl. .................. 248/129; 248/519; 248/534; 5/658

(58) Field of Classification Search ............... 248/558, 248/518, 526, 519, 535, 125.2, 125.8, 129; 414/343, 347, 349, 389, 745.2; 5/620, 81.1 R, 5/600, 658

See application file for complete search history.

(56) References Cited

U.S. PATENT DOCUMENTS

| 383,815 | A | 5/1888 | Kilborn |
|---|---|---|---|
| 1,290,809 | A | 1/1919 | Truax |
| 1,490,650 | A | 4/1924 | Wagner |
| 1,919,114 | A | 7/1933 | Ley |
| 2,470,524 | A | 5/1949 | Scudder |
| 2,497,425 | A | 2/1950 | Terry |
| 2,673,771 | A | 3/1954 | Krewson |
| 2,696,963 | A | 12/1954 | Shepherd |
| 3,004,743 | A | 10/1961 | Wenger |
| 3,213,877 | A | 10/1965 | May et al. |
| 3,431,937 | A | 3/1969 | Hettlinger et al. |
| 3,552,577 | A | 1/1971 | Latham, Jr. |
| 3,674,294 | A | 7/1972 | Kirkham |

(Continued)

FOREIGN PATENT DOCUMENTS

DE  92 04 321.6  5/1992

(Continued)

*Primary Examiner*—J. Allen Shriver, II
*Assistant Examiner*—Bradley H Duckworth
(74) *Attorney, Agent, or Firm*—Barnes & Thornburg LLP

(57) ABSTRACT

An equipment support system has a first telescoping arm and a second telescoping arm. The arms are pivotable relative to a room wall about a generally vertical axis and are extendable and retractable along respective generally horizontal axes. A first equipment support is coupled to the first telescoping arm and is configured to support patient care equipment thereon. A second equipment support is coupled to the second telescoping arm and is configured to support patient care equipment thereon.

13 Claims, 9 Drawing Sheets

U.S. PATENT DOCUMENTS

| | | | |
|---|---|---|---|
| 3,709,556 A | 1/1973 | Allard et al. | |
| 3,814,023 A | 6/1974 | Stantial | |
| 3,931,452 A | 1/1976 | Nilsson | |
| 4,005,844 A | 2/1977 | Richmond | |
| 4,094,484 A | 6/1978 | Galione | |
| 4,113,222 A | 9/1978 | Frinzel | |
| 4,190,224 A | 2/1980 | LeBlanc et al. | |
| 4,225,104 A | 9/1980 | Larson | |
| 4,262,874 A | 4/1981 | Seigh | |
| D260,816 S | 9/1981 | Zissimopoulos et al. | |
| 4,339,104 A | 7/1982 | Weidman | |
| 4,378,014 A | 3/1983 | Elkow | |
| 4,489,454 A | 12/1984 | Thompson | |
| 4,511,157 A | 4/1985 | Wilt, Jr. | |
| 4,511,158 A | 4/1985 | Varga et al. | |
| 4,559,036 A | 12/1985 | Wunsch | |
| 4,600,209 A | 7/1986 | Kerr, Jr. | |
| 4,616,797 A | 10/1986 | Cramer | |
| D289,604 S | 5/1987 | Gallant et al. | |
| 4,691,397 A | 9/1987 | Netzer | |
| 4,718,892 A | 1/1988 | Yung-Ho | |
| 4,725,027 A | 2/1988 | Bekanich | |
| 4,729,576 A | 3/1988 | Roach | |
| 4,744,536 A | 5/1988 | Bancalari | |
| 4,756,706 A | 7/1988 | Kerns et al. | |
| 4,795,122 A | 1/1989 | Petre | |
| 4,801,815 A | 1/1989 | Biette et al. | |
| 4,879,798 A | 11/1989 | Petre | |
| 4,892,279 A | 1/1990 | Lafferty et al. | |
| 4,901,967 A | 2/1990 | Petre | |
| 4,905,882 A | 3/1990 | Ross | |
| 4,905,944 A | 3/1990 | Jost et al. | |
| 4,925,444 A | 5/1990 | Orkin et al. | |
| 4,945,592 A | 8/1990 | Sims et al. | |
| 4,966,340 A | 10/1990 | Hunter | |
| 4,969,768 A | 11/1990 | Young | |
| 4,997,150 A | 3/1991 | Mardollo | |
| 5,016,307 A | 5/1991 | Rebar | |
| 5,072,906 A | 12/1991 | Foster | |
| 5,078,349 A | 1/1992 | Smith | |
| 5,083,807 A | 1/1992 | Bobb et al. | |
| 5,094,418 A | 3/1992 | McBarnes, Jr. et al. | |
| 5,108,064 A | 4/1992 | Kreuzer | |
| 5,110,076 A | 5/1992 | Snyder et al. | |
| 5,112,019 A | 5/1992 | Metzler et al. | |
| 5,125,607 A | 6/1992 | Pryor | |
| 5,135,191 A | 8/1992 | Schmuhl | |
| 5,149,036 A | 9/1992 | Sheehan | |
| 5,186,337 A | 2/1993 | Foster et al. | |
| 5,207,642 A | 5/1993 | Orkin et al. | |
| 5,219,139 A | 6/1993 | Hertzler et al. | |
| 5,224,681 A | 7/1993 | Lundstrom | |
| 5,306,109 A | 4/1994 | Kreuzer et al. | |
| 5,319,816 A | 6/1994 | Ruehl | |
| 5,326,059 A | 7/1994 | Pryor et al. | |
| 5,366,191 A | 11/1994 | Bekanich | |
| 5,400,995 A | 3/1995 | Boyd | |
| 5,407,163 A | 4/1995 | Kramer et al. | |
| 5,421,548 A | 6/1995 | Bennett et al. | |
| 5,479,958 A | 1/1996 | Kummerfeld | |
| 5,527,125 A | 6/1996 | Kreuzer et al. | |
| 5,588,166 A | 12/1996 | Burnett | |
| 5,618,090 A | 4/1997 | Montague et al. | |
| 5,636,823 A | 6/1997 | Boyd | |
| 5,647,491 A | 7/1997 | Foster et al. | |
| 5,657,884 A | 8/1997 | Zilincar, III | |
| 5,699,988 A | 12/1997 | Boettger et al. | |
| 5,704,577 A | 1/1998 | Gordon | |
| 5,857,685 A | 1/1999 | Phillips et al. | |
| 5,878,536 A | 3/1999 | Demmitt et al. | |
| 5,898,961 A | 5/1999 | Ambach et al. | |
| 5,924,658 A | 7/1999 | Shiery et al. | |
| 5,966,760 A | 10/1999 | Gallant et al. | |
| 5,987,670 A | 11/1999 | Sims et al. | |
| 6,056,249 A | 5/2000 | Fillon, Jr. | |
| 6,095,468 A | 8/2000 | Chirico et al. | |
| 6,152,426 A | 11/2000 | Von Fange | |
| 6,155,743 A | 12/2000 | Chen | |
| 6,170,102 B1 | 1/2001 | Kreuzer | |
| 6,179,260 B1 | 1/2001 | Ohanian | |
| 6,182,662 B1 | 2/2001 | McGhee | |
| 6,213,481 B1 | 4/2001 | Marchese et al. | |
| 6,431,515 B1 | 8/2002 | Gampe et al. | |
| 6,434,329 B1 | 8/2002 | Dube et al. | |
| 6,553,587 B1 | 4/2003 | Barker et al. | |
| 6,725,483 B2 | 4/2004 | Gallant et al. | |
| 7,040,057 B2 | 5/2006 | Gallant et al. | |
| 7,065,811 B2 | 6/2006 | Newkirk et al. | |
| 7,065,812 B2 | 6/2006 | Newkirk et al. | |
| 7,073,765 B2 | 7/2006 | Newkirk | |
| 7,216,382 B2 | 5/2007 | Newkirk et al. | |
| 2003/0014817 A1 | 1/2003 | Gallant et al. | |
| 2004/0164220 A1 | 8/2004 | Newkirk et al. | |
| 2004/0199996 A1 | 10/2004 | Newkirk et al. | |
| 2005/0000019 A1 | 1/2005 | Newkirk et al. | |
| 2006/0031989 A1 | 2/2006 | Graham et al. | |
| 2006/0207025 A1 | 9/2006 | Newkirk et al. | |
| 2006/0207026 A1 | 9/2006 | Newkirk et al. | |
| 2006/0226333 A1 | 10/2006 | Newkirk | |
| 2006/0242763 A1 | 11/2006 | Graham et al. | |

FOREIGN PATENT DOCUMENTS

| | | |
|---|---|---|
| DE | 92 04 3216 U1 | 7/1992 |
| EP | 0 215 212 A | 3/1987 |
| EP | 0 257 299 A | 3/1988 |
| EP | 0 943 306 B1 | 9/1999 |
| EP | 1 243 900 A2 | 9/2002 |
| FR | 1292174 A | 3/1987 |
| GB | 1 061 383 | 3/1967 |
| WO | WO 00/09061 | 2/2000 |

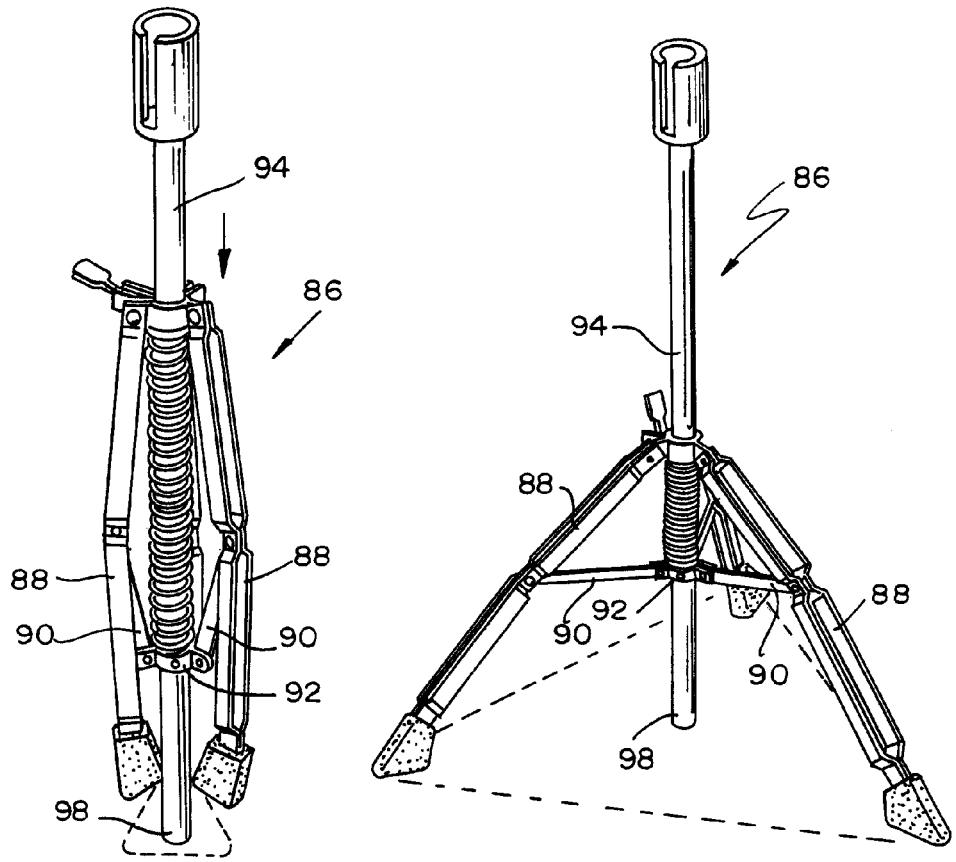
FIG. 10
FIG. 11
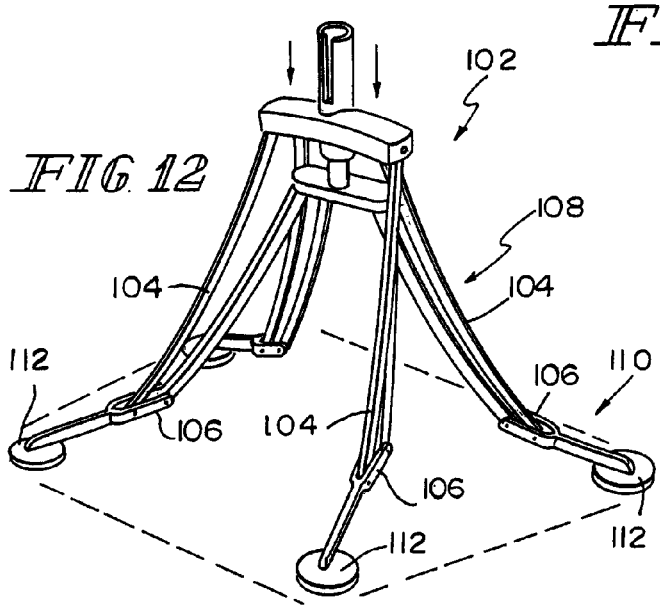
FIG. 12
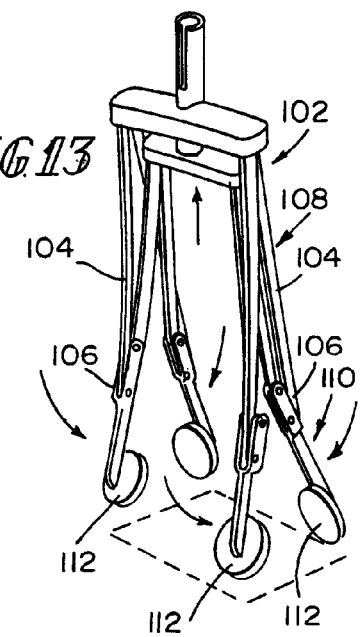
FIG. 13

PATIENT CARE EQUIPMENT MANAGEMENT SYSTEM

CROSS REFERENCE TO RELATED APPLICATIONS

This application is a continuation of U.S. patent application Ser. No. 11/422,476, filed Jun. 6, 2006, now U.S. Pat. No. 7,216,382, which is hereby incorporated by reference herein, and which is a continuation of U.S. patent application Ser. No. 10/802,289, filed Mar. 17, 2004, now U.S. Pat. No. 7,065,812, which is hereby incorporated by reference herein. U.S. patent application Ser. No. 10/802,289 claimed priority under 35 U.S.C. 119(e) to U.S. Provisional Application Ser. No. 60/455,621, filed Mar. 18, 2003 and U.S. Provisional Application Ser. No. 60/510,756, filed Oct. 13, 2003, which are hereby expressly incorporated by reference herein.

BACKGROUND OF THE INVENTION

The present disclosure relates to a system for supporting patient care equipment adjacent a patient support.

Hospitalized patients often require patient care equipment to be in close proximity during care. Such patient care equipment may include heart monitoring equipment, medical gas delivery equipment, infusion pumps, intra-venous bags, equipment monitors, defibrillators, and other patient care equipment, many of which directly connect to the patient via lines or tubes.

SUMMARY OF THE INVENTION

The present invention comprises one or more of the following features or elements in the appended claims or combinations thereof. A patient care equipment management system comprises an equipment support. The equipment support may be mountable on an arm that extends from a wall, on a column depending from the arm, on a wall mount, on a stand, or on a patient support. Various methods may be used to move the equipment support upwardly and downwardly to engage and disengage the equipment support from supporting devices.

A patient support typically has a base on the floor and a patient-support portion that is supported above the base and movable relative to the base between a first position and a second position that is lower than the first position. A support arm can be coupled to the patient-support portion, and the equipment support can be coupled to the other end of the support arm. The equipment support can be coupled to a stand. The stand may comprise a set of legs movable between a storage position and a use position, the legs being automatically deployed to the use position when the stand is lowered onto the floor.

The support arm may be a motorized lift. The support arm may have actuator buttons that operate a linear actuator. The equipment support may have a post. A post receiver may be mounted on a distal end of the support arm. A post receiver may also be mounted on a patient support frame member, on a column supported by a wall-mounted arm, on a wall mount, or on a stand.

It should be understood that while the illustrated method of coupling the equipment support to either the patient support frame member, column, wall mount, or stand shows a post mating with a post receiver, other coupling methods are within the scope of the disclosure. Therefore, it should be understood that when references to a post and a post receiver are used throughout the disclosure, such references are merely the illustrated embodiment, and in general, a first coupler may couple with a second coupler to form a support or engagement between the equipment support and the patient support frame member, the column of an arm, the wall mount, or the stand.

Additional features will become apparent to those skilled in the art upon consideration of the following detailed description of illustrative embodiments exemplifying the best mode of carrying out various systems for transporting and supporting patient care equipment as presently perceived.

BRIEF DESCRIPTION OF THE DRAWINGS

The detailed description particularly refers to the accompanying figures, in which:

FIG. 10 is a perspective view of a self-deploying stand for carrying an equipment support;

FIG. 11 is a perspective view similar to that of FIG. 10, showing the stand deployed;

FIG. 12 is a perspective view of a stand having a plurality of two-member upper legs connected to single-member lower legs;

FIG. 13 is a perspective view of the stand of FIG. 12 in the collapsed state;

DETAILED DESCRIPTION OF THE DRAWINGS

Figure 1:
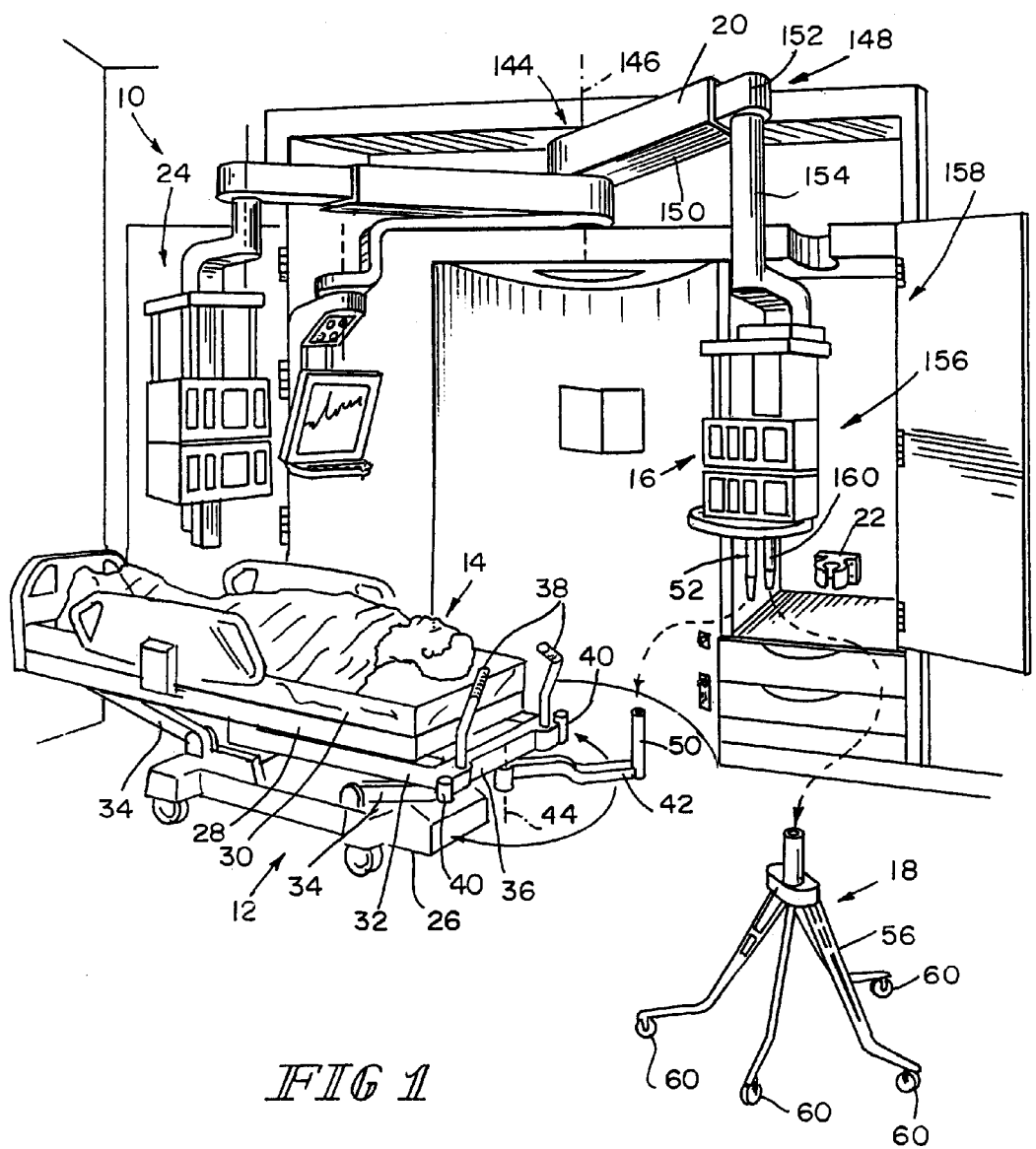
FIG. 1 is a perspective view of an equipment management system having an equipment support and patient care equipment configured to be mounted in a plurality of locations.

A patient care equipment management system 10, shown in FIG. 1, comprises an equipment support 16 that can be carried or supported by at least one of a patient support 12, a stand 18, a support arm 20, and a wall mount 22. Illustratively, equipment support 16 can be supported interchangeably by patient support 12, stand 18, support arm 20, and wall mount 22.

It should be understood that although patient support 12 is illustratively shown in FIG. 1 as a transportable hospital bed for supporting patient 14, other patient supports are within the scope of the disclosure and can be substituted for the illustrated embodiment. For example, patient support 12 could be a stretcher, a surgical table, a wheel chair, or any other medical device on which a patient may be supported.

Illustratively, equipment support 16 carries a display and a plurality of monitors for monitoring the status of patient 14. However, it should be understood that other medical devices may be carried by or incorporated into equipment support 16 as desired for the care of patient 14. An additional equipment support 24 may be provided, as can be seen in FIG. 1, and may or may not have the features described herein.

Patient support 12 illustratively includes a base 26 (typically including a base frame hidden in whole or in part by a shroud), a patient-support deck 28 supporting a mattress 30, and an intermediate frame 32. Linkage 34 connects intermediate frame 32 to base 26; the linkage 34 is power driven thereby permitting movement of patient-support deck 28 and intermediate frame 32 relative to base 26. Intermediate frame 32 illustratively includes head-end frame member 36, which is configured to extend horizontally beyond the periphery of patient-support deck 28 such that certain items can be mounted thereon, including, for example, push handles 38 and corner bumpers 40, as shown in FIG. 1. Patient support 12 has a longitudinal axis.

It will be appreciated that such patient supports or hospital beds are well known and need not be discussed in detail herein. For example, U.S. Pat. No. 5,790,997 to Weismiller discloses such a patient support and is incorporated herein by reference.

Push handles 38 are illustratively configured to respond to urges from a caregiver, including pushing or pulling forces exerted on handles 38. Such pushing or pulling of handles 38 causes handles 38 to act upon respective force sensors interposed between handles 38 and frame member 36. The force sensors may comprise, for example, load cells (not shown) that are housed in patient support 12 and that sense the force applied to handles 38. The load cells send signals to a motorized traction device (not shown) for propelling the patient support 12, as is disclosed further in U.S. Publication Number 2002/0088055 A1, incorporated herein by reference. However, it should be understood that push handles 38 may alternatively comprise standard-mount handles, or push handles 38 may be omitted from patient support 12.

Figure 2:
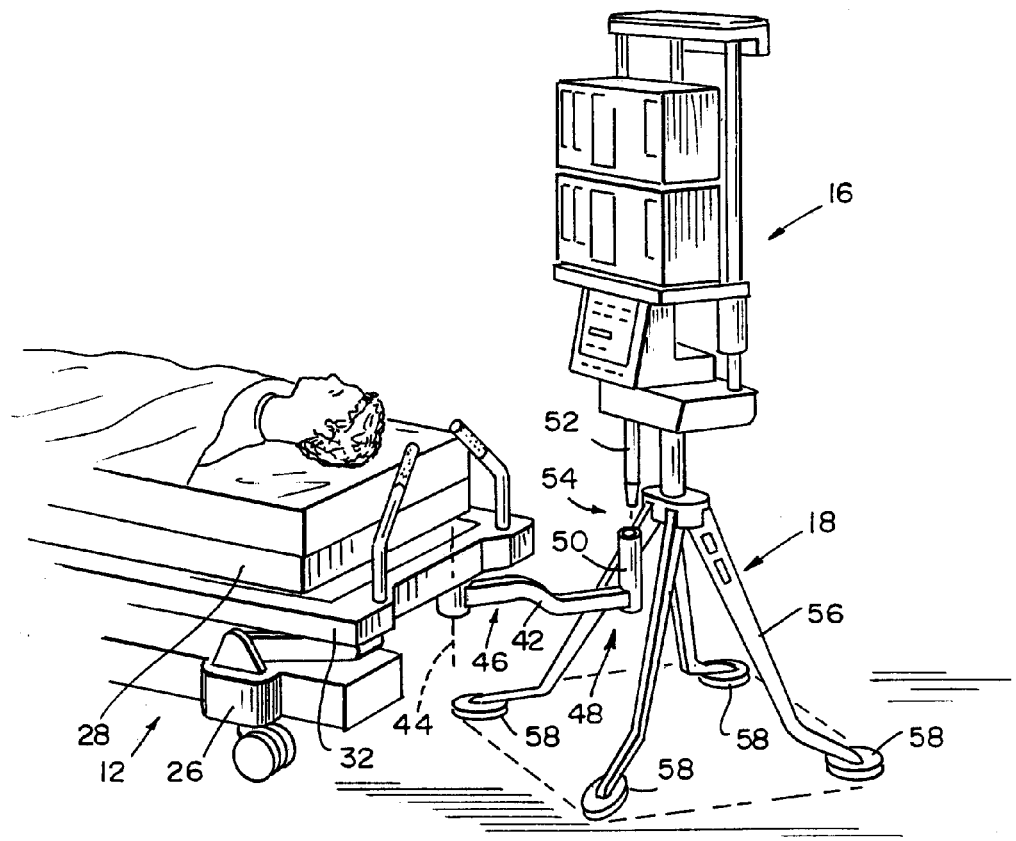
FIG. 2 is a perspective view of the equipment support positioned on a stand adjacent to a patient support.
Figure 3:
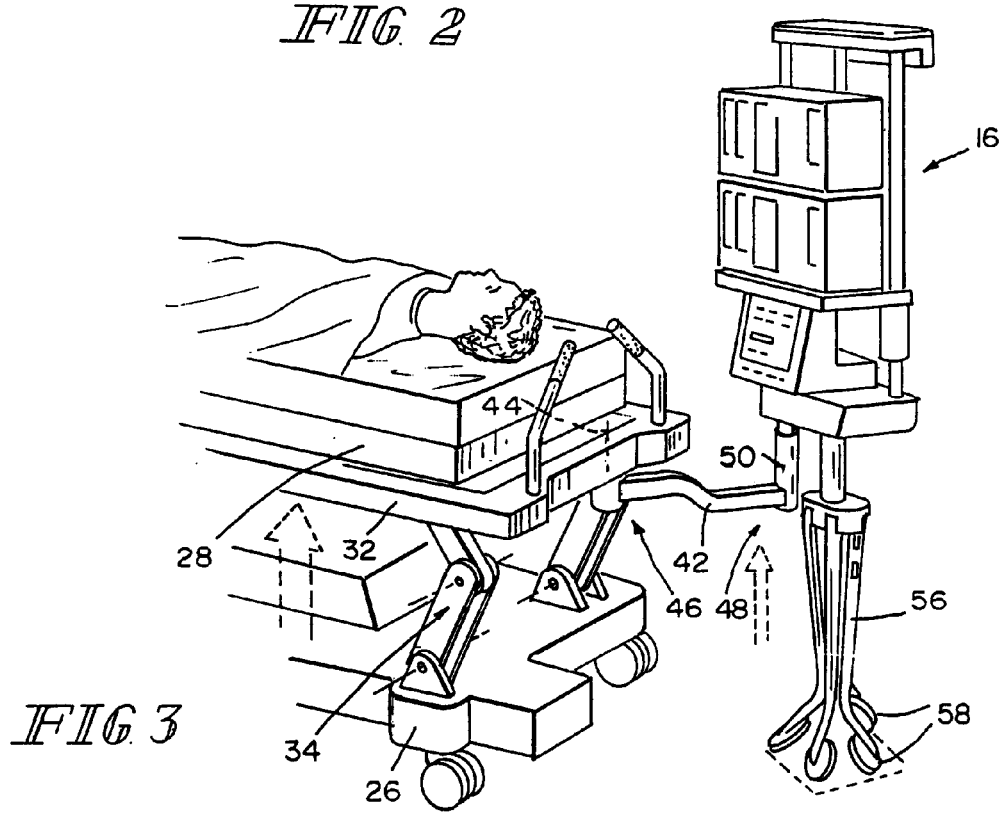
FIG. 3 is a perspective view similar to that of FIG. 2 showing the equipment support carried by an arm extending from the patient support.

An engager, such as illustrative support arm 42, can be mounted to frame member 36, as shown in FIGS. 1-3. Support arm 42 is illustratively pivotably mounted to frame member 36 such that support arm 42 pivots about axis 44. It should be understood, however, that other constructions for pivotably mounting support arm 42 to frame member 36 are within the scope of the disclosure.

The illustrative manner in which support arm 42 engages and supports equipment support 16 is shown in FIG. 2. Support arm 42 illustratively includes a proximal end 46 that is coupled to frame member 36 and a distal end 48 that is spaced apart from proximal end 46. A post receiver 50 is illustratively mounted to distal end 48 of support arm 42. Post receiver 50 is configured to engage a downwardly pointing post 52 located on equipment support 16. Illustratively, post 52 is conical frustum shaped at lower end 54, facilitating engagement between post receiver 50 and post 52 even when alignment between the two is slightly off. It should be understood, however, that other approaches by which support arm 42 engages and supports equipment support 16 are within the scope of the disclosure. For example, support arm 42 could have a post mounted on distal end 48, while equipment support 16 could have a post receiver. Or as discussed above, support arm 42 could have a first coupler and equipment support could have a second, corresponding coupler.

FIG. 3 shows the illustrated embodiment of the support arm 42 engaging and supporting equipment support 16. Post receiver 50 on distal end 48 of support arm 42 is brought into engagement with lower end 54 of post 52 by raising patient-support deck 28 and intermediate frame 32 relative to base 26. As intermediate frame 32 raises relative to base 26, support arm 42 raises with frame member 36 and intermediate frame 32, thereby moving post receiver 50 toward engagement with post 52.

Once post 52 and post receiver 50 are mated together, as shown in FIG. 3, support arm 42 can fully support equipment support 16, and collapsible legs 56 of stand 18 need not balance nor support the weight of equipment support 16. Therefore, as support arm 42 continues to raise with intermediate frame 32, legs 56 begin to draw in closer toward each other as a result of the force of gravity pulling the legs downwardly, as can be seen in FIG. 3.

Figure 14:
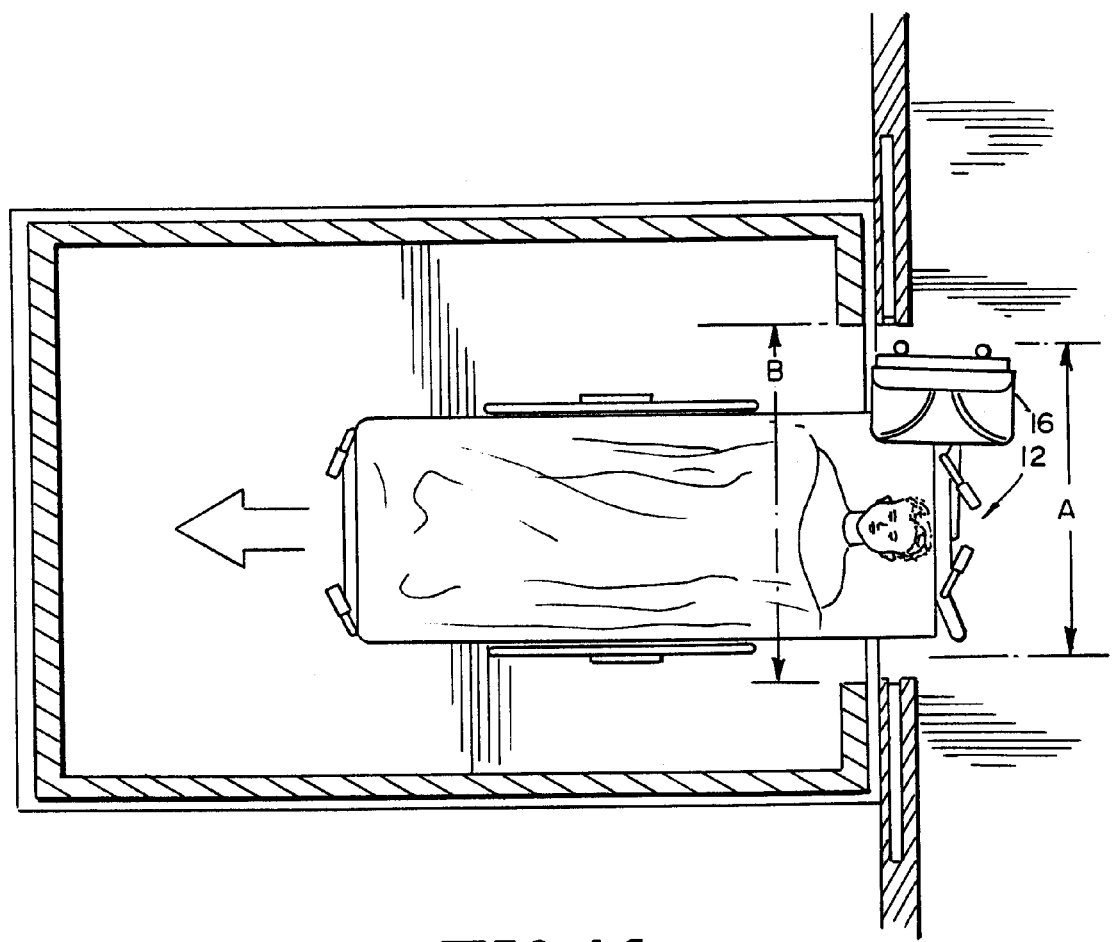
FIG. 14 is a top view of an equipment support mounted on a patient support so as to permit passage through an elevator door.

As discussed above, support arm 42 is pivotably mounted to frame member 36, and is pivotable between a substantially longitudinally extending position relative to the patient support, shown in FIGS. 2-3, and a substantially laterally extending position, as shown in FIG. 14. Furthermore, as can be seen in FIGS. 2-3, support arm 42 has a stepped configuration and is formed such that distal end 48 of support arm 42 is lower in elevation than proximal end 46 of support arm 42. Such pivotable mounting permits distal end 48 of support arm 42 to pivot to a position below patient support deck 28, allowing equipment support 16 to be brought in sufficiently close to a side of patient support 12 such that equipment support 16 and patient support 12 having a width A can fit into an elevator door having a width B (commonly a standard of 48" wide) as shown in FIG. 14. During transport, legs 56 are illustratively lifted a sufficient height off of the floor such that elevator and door thresholds can be cleared during transport without contacting legs 56.

When it is desirable to again return equipment support 16 to a position supported on the floor, for example when patient support 12 has reached the anticipated destination, patient-support deck 28 is lowered in relation to base 26, and likewise intermediate frame 32 and frame member 36 lower with patient-support deck 28. Support arm 42 lowers as frame member 36 lowers, and foot pads 58 on legs 56 contact the floor.

In one illustrative embodiment, when foot pads 58 contact the floor, an outer edge of each foot pad 58 contacts first, urging foot pads 58 and their respective legs 56 outwardly toward the deployed position, shown in FIG. 2. Eventually, post receiver 50 disengages from post 52 after frame 32 is lowered by a sufficient amount, leaving equipment support 16 free-standing, as can be seen in FIG. 2.

In the disclosed embodiment, foot pads 58 each include a castor wheel (not shown) housed in the foot pad 58. The castor wheel is disclosed to be near the outer edge of the foot pad 58 such that it is the first to contact the floor when equipment support 16 is lowered from its transport position, thereby facilitating deployment of the legs 56. However, it is within the scope of the disclosure to utilize synthetic footpads comprised of a material that glides over the floor, rather than having footpads with castor wheels. Alternatively, castors 60 may be substituted for the foot pads, as can be seen in FIG. 1. Legs 56 may or may not be collapsible.

Figure 4:
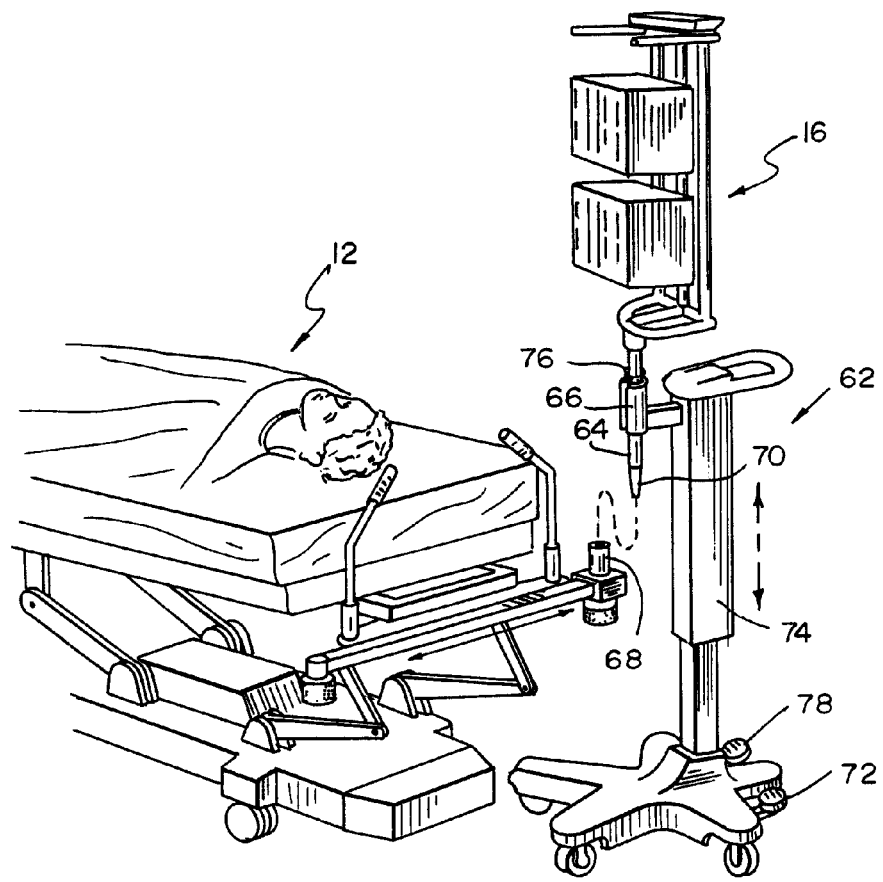
FIG. 4 is another perspective view of the equipment support positioned on a vertically telescoping stand.

FIGS. 4-13, 15 and 16 show alternative embodiments of various elements of an equipment management system. FIG. 4 shows a mount post 64 (see post 64 in FIG. 16 as well) that extends below equipment support 16 to engage a post receiver 66 on stand 62. Illustratively, patient support device 12 also includes a post receiver 68 configured to receive end 70 of mount post 64. When it is desired to position equipment support 16 on patient support device 12 and disconnect support 16 from stand 62, end 70 is positioned over post receiver 68 and release pedal 72 is depressed on the base of stand 62. End 70 of mount post 64 is illustratively conical frustum shaped. Release pedal 72 illustratively releases a pneumatic piston inside telescoping column 74 of stand 62, thereby allowing for column 74 to retract under its own weight so that end 70 of mount post 64 can engage an aperture formed in post receiver 68.

Figure 15:
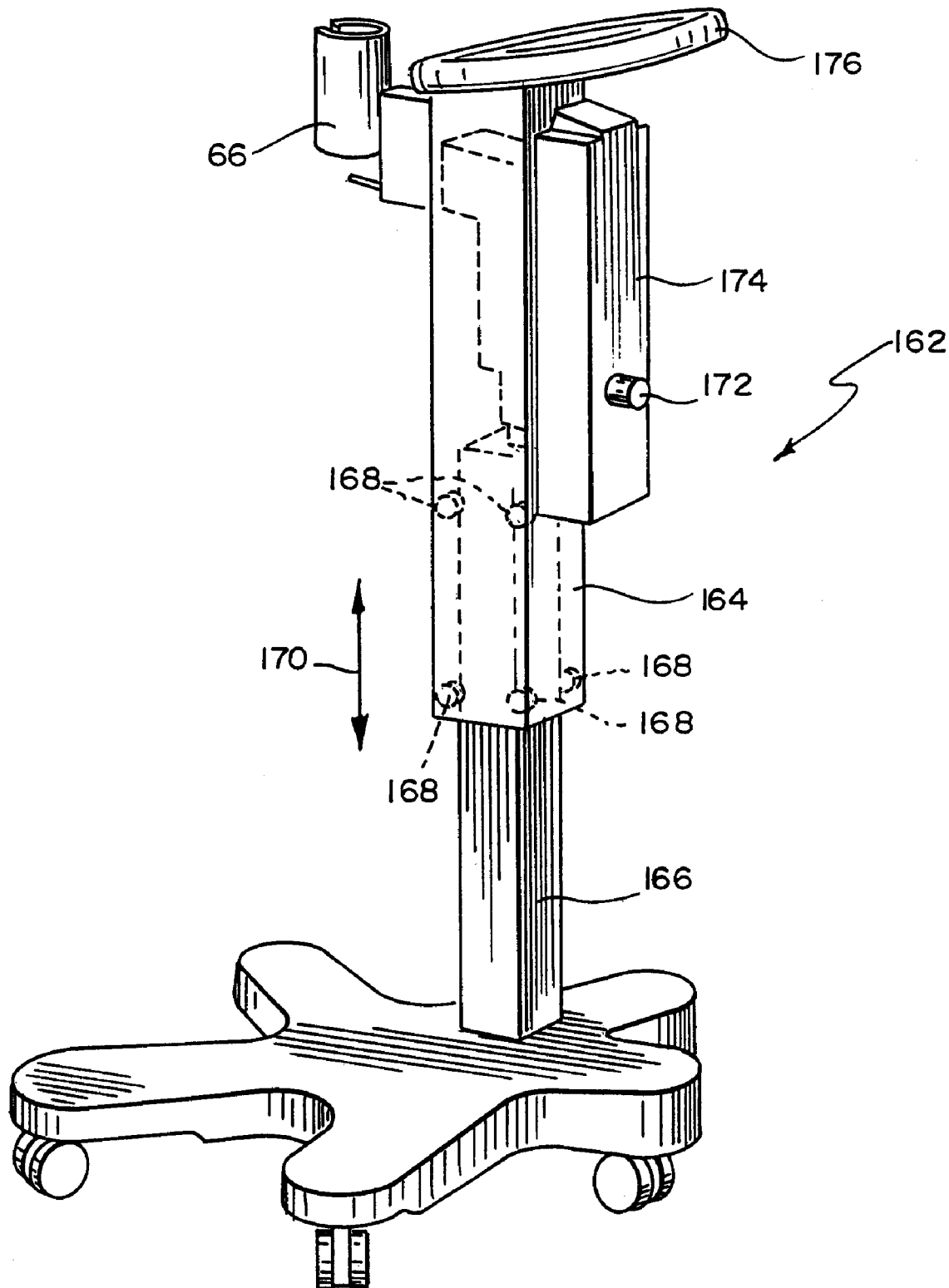
FIG. 15 is another embodiment of a telescoping stand.
Figure 16:
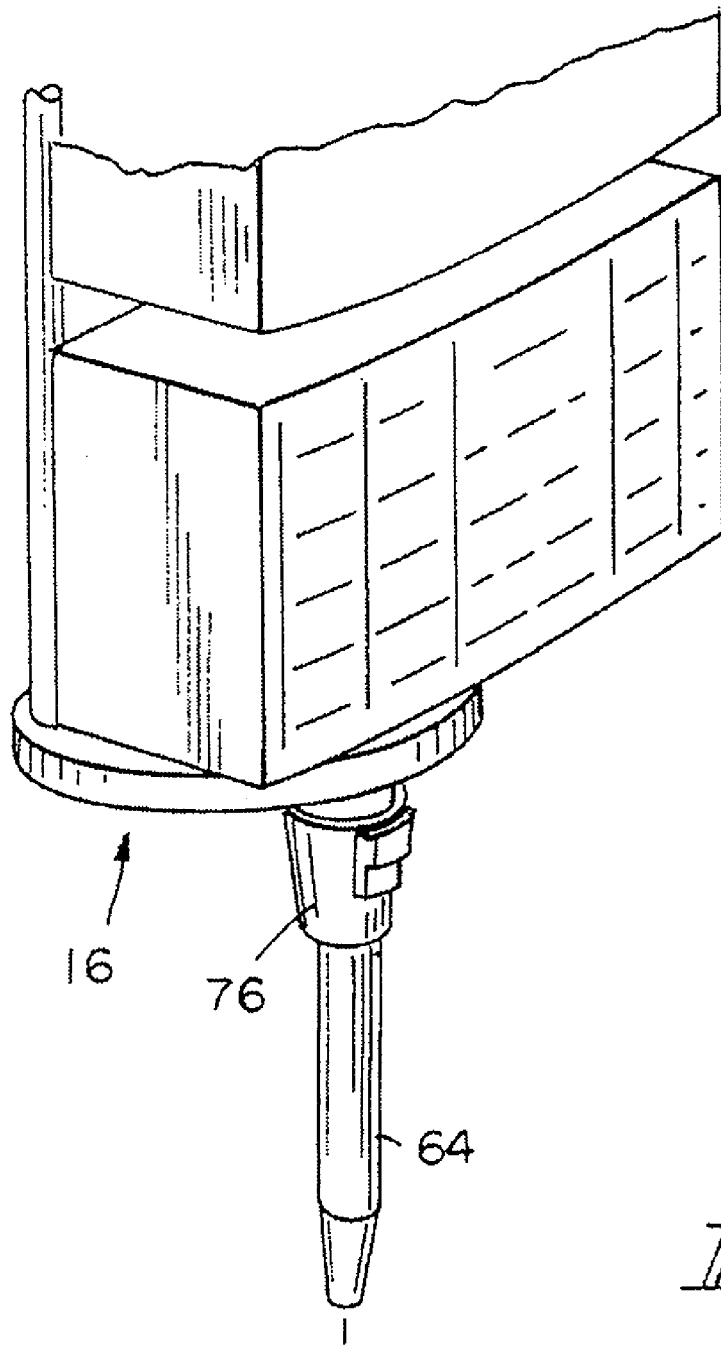
FIG. 16 is a perspective view of a portion of the equipment support of FIG. 4.

Another embodiment of a telescoping stand 162 is illustrated in FIG. 15. Illustratively, stand 162 comprises a telescoping column 164 that telescopes relative to base 166. A bearing system having bearings 168 facilitates telescoping movement in the direction of arrow 170. A control pendant (not shown) can be attached with a cord, the control pendant actuating telescoping movement of the stand 162. An emergency stop button 172 is disclosed for overriding or halting the telescoping movement. In the disclosed embodiment, a Linak LA 31 linear actuator is housed internally in the telescoping column 164, and a Linak "Jumbo" battery pack and Linak "Jumbo" control box are positioned inside housing 174, mounted on the exterior of telescoping column 164. Illustratively, telescoping stand 162 may have between 30.48 and 45.72 cm of telescoping movement. A handle 176 is also provided for horizontal movement of stand 162.

Post receiver 66, as seen in FIGS. 4 and 15, illustratively comprises a substantially C-shaped cross-section that permits the passage of end 70 (shown in FIG. 4) therethrough, while being capable of engaging a collar 76 (see collar 76 in FIG. 16 as well) on mount post 64. Therefore, once end 70 is in place, post receiver 66 of stand 62 can be lowered below collar 76 and disengaged from mount post 64, permitting stand 62 to be moved away from patient support device 12. It should be understood that other embodiments and coupling mechanisms are within the scope of the disclosure, including the use of a protrusion instead of a collar.

Post receiver 68 may be fixedly mounted on a patient support 12, or it may be horizontally movable relative to the patient support 12. Post receiver 68 may be located at any number of positions, including at the side, head end, center, or corner of patient support 12.

When it is desired to again position equipment support 16 on stand 62, post receiver 66 can engage end 70 below collar 76, and lift pedal 78 can be actuated (illustratively pumped up and down) to extend telescoping column 74 upwardly to engage collar 76, lifting equipment support 16 off of patient support device 12.

Figure 5:
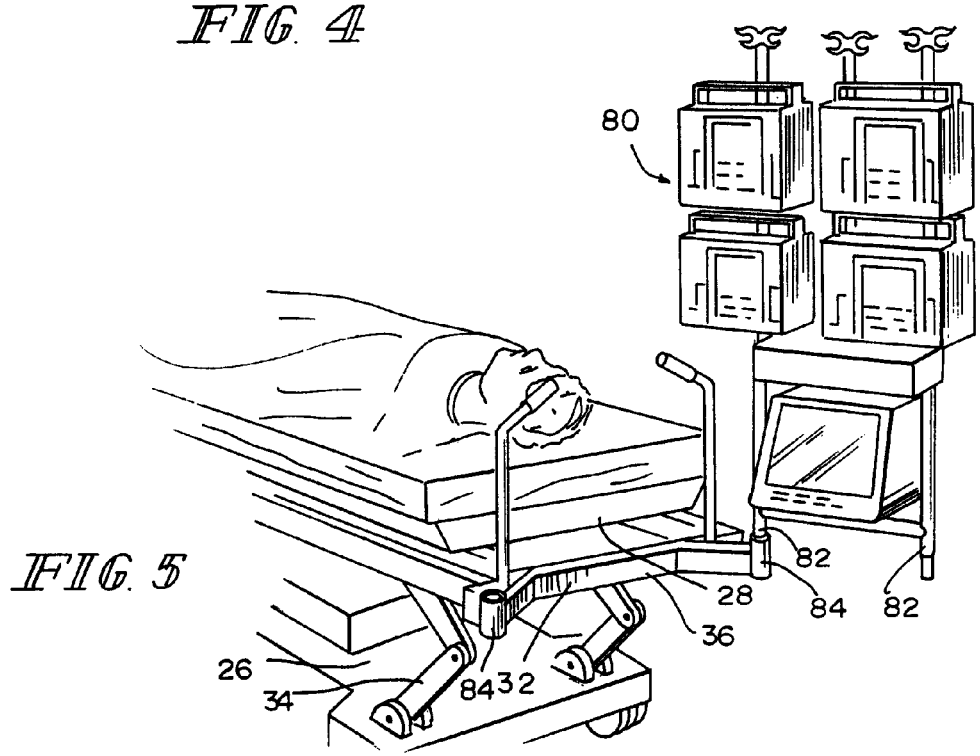
FIG. 5 is a perspective view of another equipment support having two posts for mounting on post receivers.
Figure 6:
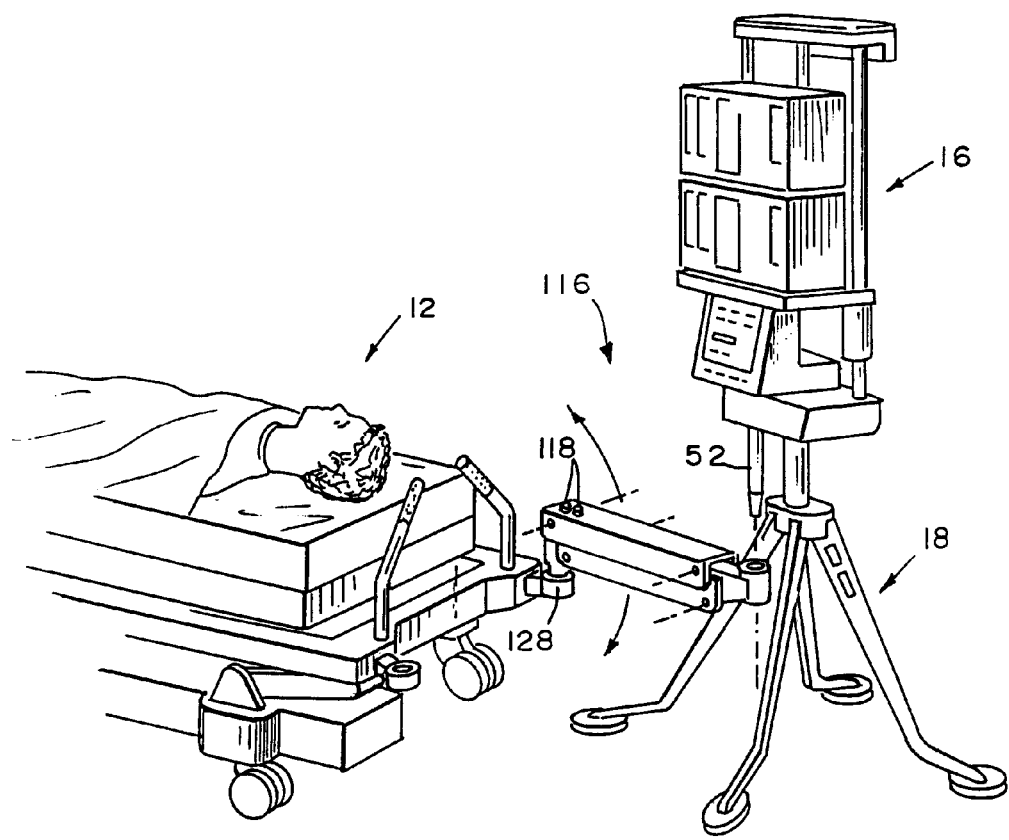
FIG. 6 is a perspective view of an equipment support that is supportable by a motorized lift configured to engage a post of the equipment support.
Figure 7:
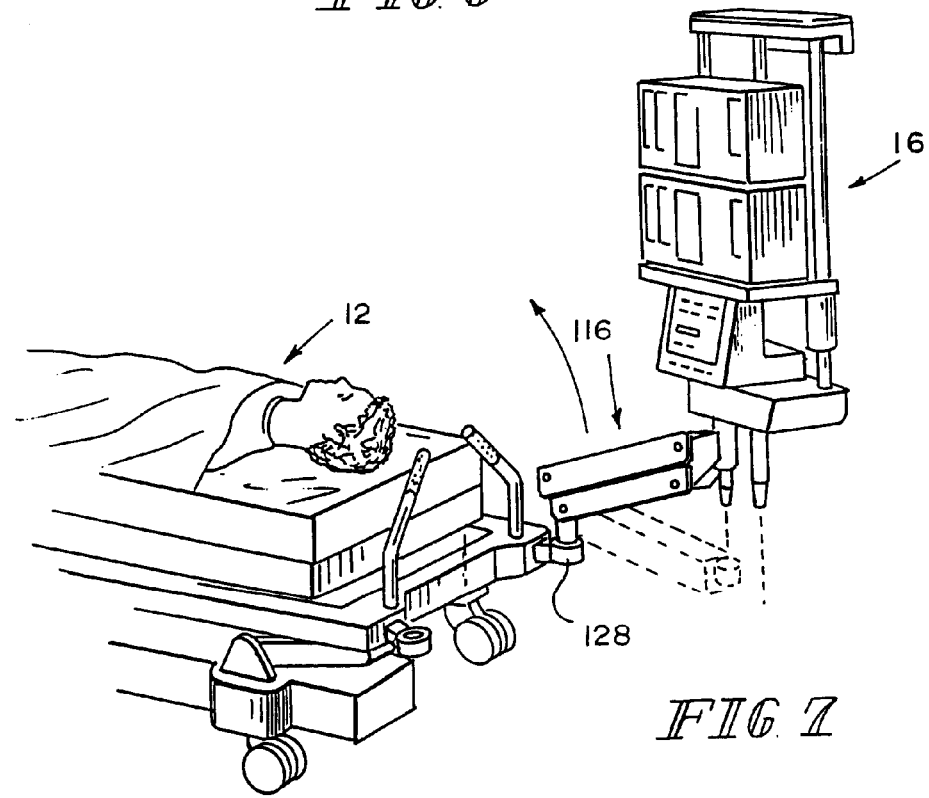
FIG. 7 is a perspective view similar to that of FIG. 6 showing the motorized lift engaged with the equipment support post.

FIG. 5 shows an equipment support 80 having two posts 82 configured to mate with post receivers 84 coupled to frame member 36. Illustratively, a selected one of posts 82 is inserted into a selected post receiver 84, and is pivotable about an axis coaxial with the selected post 82.

It should be understood that while the illustrative embodiments show post receivers on a head end of a patient support, it is within the scope of the disclosure to mount post receivers on other portions of the bed for equipment support placement at a side or foot end of a bed. It is also within the scope of the disclosure to utilize a plurality of post receivers simultaneously—for either multiple equipment supports or for an equipment support that comprises spaced apart posts that simultaneously are supported by equally spaced apart post receivers.

In still another embodiment, a support arm can have an elbow or pivot joint (not shown) for further range of motion of a supported equipment support 16 about a second parallel axis.

FIGS. 10-13 show additional embodiments of a stand. FIGS. 10-11 show a stand 86 having a plurality of legs 88 linked via linkage 90 to a central hub 92. Central hub 92 is configured to slide vertically on a centrally located post 94, and is biased toward the transport position by spring 96. A deployment-assist tube 98 is sleeved over post 94, such that post 94 and tube 98 are coaxial. Deployment of legs 88 occurs in the following fashion. As a result of the bias of spring 96, legs 88 remain in their transport position, shown in FIG. 10, unless outside forces act upon stand 86. When it is desired to deploy legs 88, stand 86 is pushed toward the floor such that deployment-assist tube 98 contacts the floor and begins to move axially relative to post 94. Such axial movement of tube 98 relative to post 94 causes tube 98 to urge hub 92 vertically upwardly on post 94, thereby moving linkage 90, as can be seen in FIG. 11. Each linkage 90 is pivotably mounted on one end to hub 92, and on the other end to a central portion of a leg 88. In the deployed position, shown in FIG. 11, stand 86 is maintained in the deployed position by the weight of the equipment support that would be mounted on stand 86. Once equipment support is lifted, legs 88 withdraw to the transport position as a result of the bias of spring 96. Foot pads 100 may be castors, rubber feet, slidable polymeric pads, or any other foot pad known in the art.

FIGS. 12-13 show another embodiment for a stand 102. Stand 102 comprises a plurality of legs 104, each leg 104 having a four-bar linkage including a knee joint 106. Each leg 104 has a two-member upper portion 108 connected at knee joint 96 to a single-member lower portion 110. By spacing apart the connection of the two members to the single member, legs 104 of stand 102 extend farther out when deployed, covering a larger footprint with comparatively shorter legs.

Illustratively, foot pads 112 coupled to distal ends of legs 104 have a polymeric composition, and are configured to slide relative to the floor and thereby facilitate the deployment of legs 104 when foot pads 112 come into contact with the floor.

Another embodiment for a support arm 114 extending from a patient support 12 is shown in FIGS. 6-9. Such an embodiment can be used on any patient support, but is particularly useful on patient supports 12 having fixed intermediate frames that do not move relative to the base of the patient support 12 and that may carry headboards (not shown). In such an embodiment, a 4-bar motorized lift 116 is provided, the lift 116 illustratively having actuator buttons 118 located thereon which can be depressed by a caregiver desiring to either lower or raise equipment support 16 relative to patient support 12.

Figure 8:
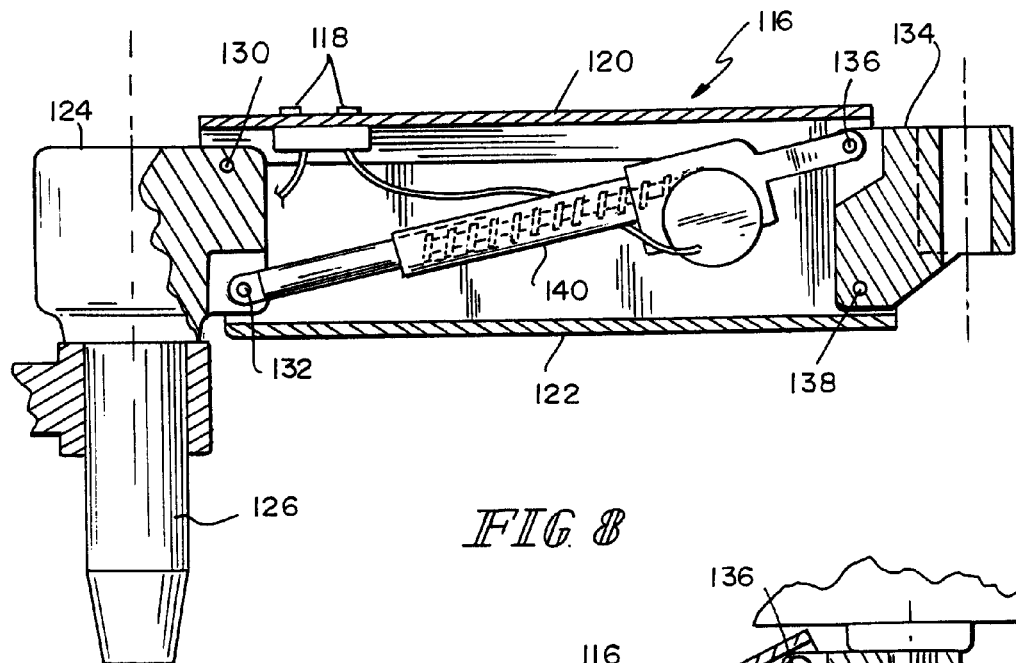
FIG. 8 is a cross-sectional view of the motorized lift of FIGS. 6-7 showing a linear actuator housed therein.
Figure 9:
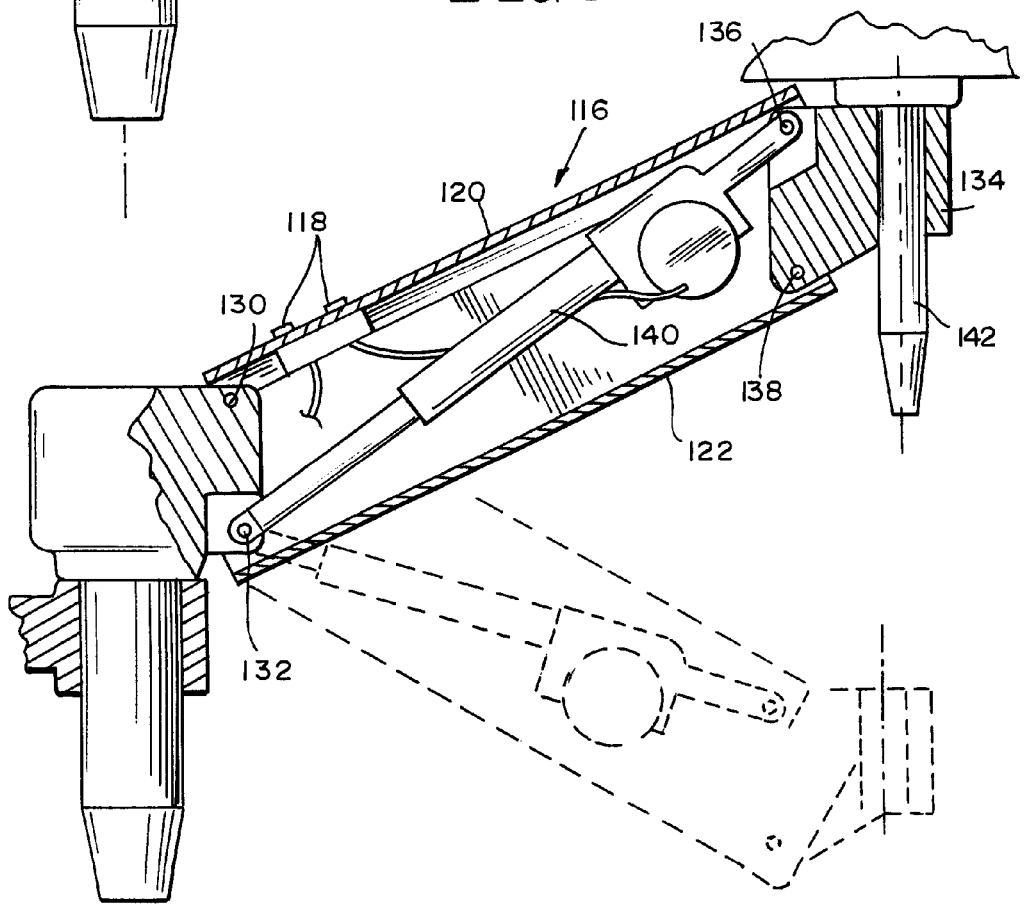
FIG. 9 is a cross-sectional view similar to that of FIG. 8 showing the linear actuator extended such that the motorized lift is in a raised position.

As shown in the cutaway views of FIGS. 8-9, motorized lift 116 comprises a top frame member 120 and a bottom frame member 122, each frame member illustratively being a U-shaped metal beam. A patient-support mount 124 illustratively includes a post 126 for insertion into a post receiver 128 (visible in FIGS. 6-7). However, it should be understood that other configurations for a patient-support mount are within the scope of the disclosure, and motorized lift 116 could alternatively be directly mounted on a frame member of patient support 12.

Frame members 120, 122 are each illustratively pivotably attached to patient-support mount 124 at one end via pins 130, 132. At the other end, frame members 120, 122 are pivotably attached to a post receiver 134 via pins 136, 138. A linear actuator 140 is illustratively coupled at one end to bottom frame member 122 via pin 132, and at the other end to top frame member 120 via pin 136. Linear actuator 140 is illustratively an electrically powered linear motor, however, it is within the scope of the disclosure to utilize any electric, pneumatic, gas powered, or other type of motor that is capable of lifting one end of a motorized lift relative to the other end. Such an illustrative linear actuator may be commercially available from Linak® as model number LA28. Linak is headquartered in Nordborg, Denmark.

Illustratively, as linear actuator 140 extends, pin 136 (and consequently post receiver 134) is moved away from pin 132 (which is connected to patient-support mount 124), therefore motorized lift 116 is moved from a lowered position, such as the phone shown in phantom in FIG. 9, to a raised position, as shown in dark lines in FIG. 9. Furthermore, because top frame member 120 and bottom frame member 122 slidably move relative to each other when linear actuator 140 is actuated, post receiver 134 is caused to remain oriented so as to provide a substantially vertical support for a post 142, as seen in FIG. 9.

As can be seen in FIG. 1, equipment support 16 can be mounted on a telescoping arm 20 that extends from a wall. Telescoping arm 20 may comprise a mount end 144 that is pivotable about a vertical axis 146, and a equipment-support end 148. Arm 120 may include a first segment 150 and a second segment 152 that telescopes horizontally into and out of segment 150. In addition to pivoting about axis 146 and telescoping horizontally, arm 20 may be configured so that equipment support 16 is rotatable relative to telescoping arm 20. Thus, arm 20 is configured such that equipment support 16 can be positioned at any location alongside patient support 12.

Equipment support 16 is illustratively mounted on a column 154 which extends downwardly from the distal end of arm 20. Lower portion 156 of column 154 is illustratively vertically movable relative to arm 20 such that equipment support 16 can be vertically raised and lowered and selectively docked on either post receiver 50, stand 18, or wall mount 22. Posts 52 and 160 of equipment support 16 can be manufactured in various sizes as required by the application. In some applications, only a single post may be required. Illustratively, wall mount 22 is C-shaped and is attached to an inner wall of cabinet 158.

The structural details of such radial arm arrangements are shown in a companion patent application entitled "Radial Arm System for Patient Care Equipment", U.S. patent application Ser. No. 10/802,287, being filed simultaneously with this application and based on U.S. Provisional Application Ser. No. 60/455,621, filed Mar. 18, 2003 (entitled "Patient Equipment Support System") and U.S. Provisional Application Ser. No. 60/510,756, filed Oct. 13, 2003 (entitled "Patient Equipment Support System"), the co-filed application being incorporated herein by reference. It will be appreciated that linear actuators or the like may be used to extend and retract the radial arm 20 to move column 154.

Although the invention has been described in detail with reference to certain illustrative embodiments, variations and modifications exist with the scope and spirit of this disclosure as described and defined in the following claims.

The invention claimed is:

1. A system for use with a hospital bed, the system comprising a patient equipment support having a first coupler which includes a collar, a conical frustum shaped portion that is lower in elevation than the collar, and a support structure that is interposed between the collar and the conical frustum shaped portion, and a stand having a wheeled base and a column extending generally vertically upwardly from the base, the stand further having a second coupler including a portion extending from the column and movable upwardly and downwardly relative to the base, the collar of the first coupler engaging the portion of the second coupler when the patient equipment support is coupled to the stand, and the first coupler being configured so that, when the collar engages the portion of the second coupler, the entire conical frustum shaped portion is exposed at a lower elevation than the collar for insertion into an aperture of a receiver of the hospital bed in response to lowering of the second coupler when the patient equipment support is coupled to the stand and the conical frustum shaped portion is aligned with the receiver, the conical frustum shaped portion being separated from the collar and supported in spaced apart relation from the collar by the support structure that is interposed between the collar and the conical frustum shaped portion and that has a vertical dimension larger than that of the conical frustum shaped portion such that a bottom of the collar is elevated with respect to a top of the conical frustum shaped portion by a vertical distance that is larger than a vertical length of the conical frustum shaped portion, the conical frustum shaped portion extending downwardly from the support structure and the collar being situated adjacent a top of the support structure, wherein the support structure interposed between the collar and the conical frustum shaped portion is devoid of any conical frustum shaped structure.

2. The system of claim 1, wherein the upward and downward movement of the second coupler relative to the base is effected by an electrically powered actuator.

3. The system of claim 2, wherein the electrically powered actuator comprises a linear actuator.

4. The system of claim 1, wherein the second coupler is movable upwardly relative to the base in response to movement of a manual input.

5. The system of claim 4, wherein the manual input comprises a pedal that is coupled to the base.

6. The system of claim 1, wherein the second coupler is movable downwardly relative to the base in response to movement of a manual input.

7. The system of claim 6, wherein the manual input comprises a pedal that is coupled to the base.

8. The system of claim 1, wherein the first and second couplers are configured so that the second coupler separates from the collar after the patient equipment support is supported by the hospital bed and the second coupler is further lowered relative to the base.

9. The system of claim 8, wherein the stand is transportable away from the patient equipment support after the patient equipment support is supported by the hospital bed.

10. The system of claim 1, wherein the patient equipment support comprises an IV rack.

11. The system of claim 9, wherein the second coupler of the patient equipment support is situated below the IV rack.

12. The system of claim 1, wherein the collar and conical frustum shaped portion of the first coupler are generally vertically aligned.

13. The system of claim 1, wherein the column of the stand comprises a telescoping column.

* * * * *